(12) United States Patent
Breeding et al.

(10) Patent No.: US 6,903,344 B2
(45) Date of Patent: Jun. 7, 2005

(54) BASELINE CORRECTION IN PET UTILIZING CONTINUOUS SAMPLING ADCS TO COMPENSATE FOR DC AND COUNT RATE ERRORS

(75) Inventors: John E. Breeding, Knoxville, TN (US); John W. Young, Knoxville, TN (US); Mark Musrock, Oak Ridge, TN (US)

(73) Assignee: CTI PET Systems, Inc., Knoxville, TN (US)

( * ) Notice: Subject to any disclaimer, the term of this patent is extended or adjusted under 35 U.S.C. 154(b) by 267 days.

(21) Appl. No.: 10/396,543

(22) Filed: Mar. 25, 2003

(65) Prior Publication Data

US 2004/0188623 A1 Sep. 30, 2004

(51) Int. Cl.[7] ............................................. G01T 1/164
(52) U.S. Cl. .................................................. 250/363.03
(58) Field of Search ..................................... 250/363.03

(56) References Cited

U.S. PATENT DOCUMENTS

| | | |
|---|---|---|
| 5,585,637 A | 12/1996 | Bertelsen et al. |
| 5,608,221 A | 3/1997 | Bertelsen et al. |
| 5,774,522 A * | 6/1998 | Warburton .................... 378/91 |
| 5,841,140 A | 11/1998 | McCroskey et al. |
| 6,072,177 A | 6/2000 | McCroskey et al. |
| 6,160,259 A | 12/2000 | Petrillo et al. |
| 6,252,232 B1 | 6/2001 | McDaniel et al. |
| 6,255,655 B1 | 7/2001 | McCroskey et al. |
| 6,291,825 B1 | 9/2001 | Scharf et al. |
| 6,822,506 B2 * | 11/2004 | Binkley ....................... 327/551 |

OTHER PUBLICATIONS

B. Yu et al., "Front–end electronics for high rate, position sensitive neutron detectors," Elsevier, Nuclear Instruments and Methods in Physics Research A, vol. 485, No. 3, (Jun. 2002) pp. 645–652.*

J. M. Rochelle et al., "Fully Integrated Current–Mode CMOS Gated Baseline Restorer Circuits," IEEE Transactions on Nuclear Science, vol. 42, No. 4 (Aug. 1995) pp. 729–735.*

Takahashi et al., A New Pulse Height Analysis System Based on Fast ADC Digitizing Technique, Conference Record of the Nuclear Science Symposium & Medical Imaging Conference, 1992, pp. 350–352, vol. 1.

* cited by examiner

Primary Examiner—Constantine Hannaher
(74) Attorney, Agent, or Firm—Pitts & Brittian, P.C.

(57) ABSTRACT

A method and apparatus for determining and correcting the baseline of a continuously sampled signal for use in positron emission tomography. The method employs continuous signal sampling to determine the signal level at time t(0) so that an accurate determination of an integrated signal may be calculated, resulting in an accurate energy estimate for an ac-coupled, continuously-sampled signal at various count rates. The device includes a front-end electronics processing channel including primarily an analog CMOS ASIC, a bank of ADCs, an FPGA-based digital sequencer, and two RAMs. The processing electronics perform continuous digital integration of PMT signals to obtain normalized position and energy. Continuous baseline restoration (BLR) is used, wherein the baseline of the signal pulses are placed at mid-scale by continuously sampling the ADC, thus always making available the past history. A correction signal is generated for use in negative feedback control of the baseline.

16 Claims, 6 Drawing Sheets

(PRIOR ART)

Fig.4

(PRIOR ART)

BASELINE CORRECTION IN PET UTILIZING CONTINUOUS SAMPLING ADCS TO COMPENSATE FOR DC AND COUNT RATE ERRORS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention pertains to the field of gamma ray detection. More specifically, the invention relates to a method for determining and correcting the baseline of a continuously sampled signal for use in positron emission tomography.

2. Description of the Related Art

Figure 1:
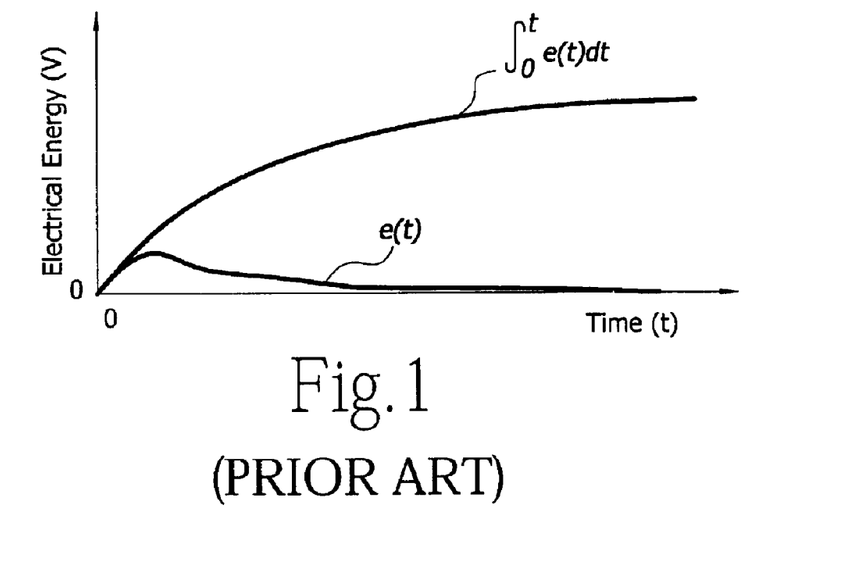
FIG. 1 is a graphical illustration of one prior art method of integrating a light signal from a crystal scintillation event in order to measure the energy absorbed from a gamma ray interacting with a detector.

In the field of positron emission tomography (PET), it is well known that to measure the energy absorbed from a gamma ray interacting in a scintillating crystal, the total light from a crystal must be determined by integrating the photomultiplier tube (PMT) current. This current signal represents the rate of light collected by the sensing PMTs or photodiodes. The integration to determine the total light is traditionally performed using analog circuitry via a gated integrator. This method is graphically illustrated in FIG. 1. Shown are the PMT current signal i(t) from a scintillation event and the integration of the current signal i(t), or:

$$e(t) = \int_0^t i(t) dt$$

It will be understood by those skilled in the art that either voltage signals or current signals may be measured.

Figure 2:
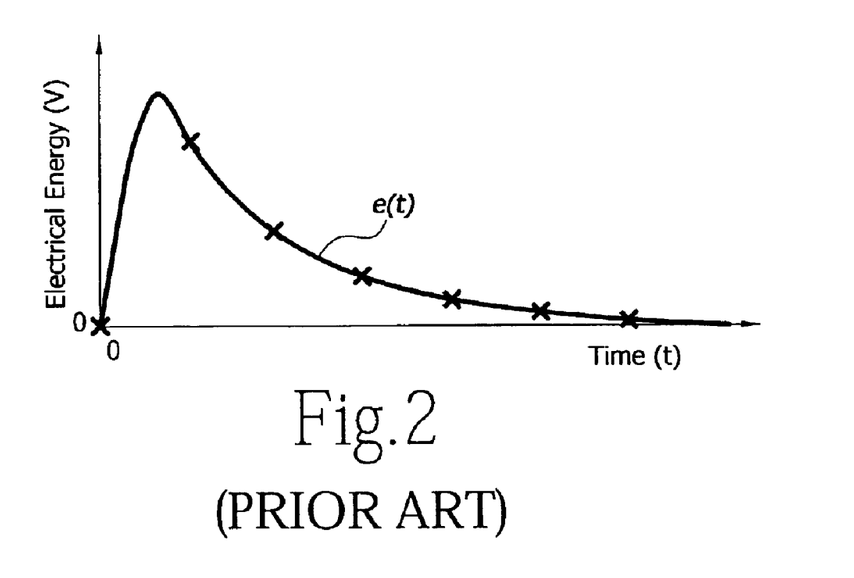
FIG. 2 is a graphical illustration of an alternate prior art method of integrating a light signal from a crystal scintillation event.

Alternately, as graphically illustrated in FIG. 2, the integration may be performed by using a uniformly weighted summation of digital samples of the signal. In this method, the level of the signal at time t(0) is precisely at zero volts. However, when the PMT signal is AC-coupled to an analog-to-digital converter (ADC), the level at time t(0) is not zero volts, but varies with the count rate and electronic offset errors.

Figure 3:
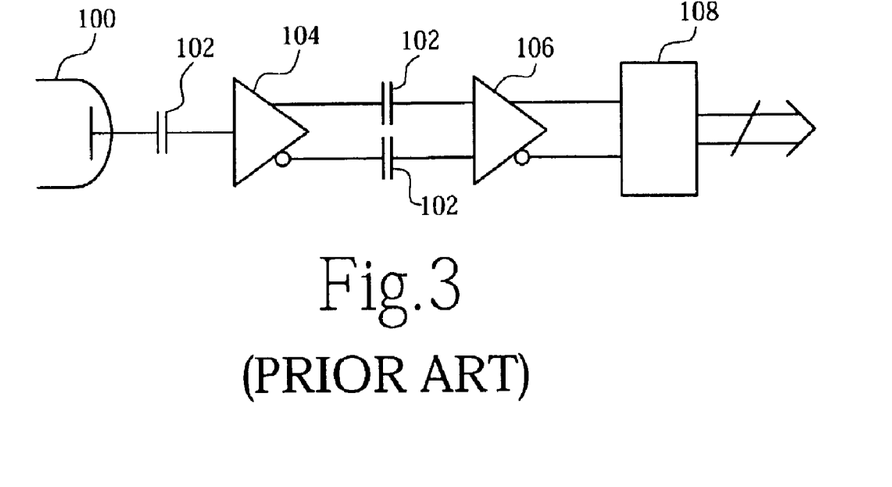
FIG. 3 is a schematic diagram of prior art circuitry incorporating isolation capacitors due to a high voltage bias of a PMT and to reduce DC offset errors.

A gamma ray from an annihilation event interacts with a scintillator crystal, which produces a light output sensed by a PMT. For pulse applications, it is advantageous to use positive bias at the PMT, which results in high voltage bias applied to the anode contact of the PMT. To isolate the processing electronics, AC coupling is required between the PMT and the preamplifier stage. AC coupling between multistages reduces the DC offset errors that accumulate throughout the data processing chain. In the schematic illustration of FIG. 3, an isolation capacitor 102 is disposed between the PMT 100 and a pre-amplifier 104 because of the high voltage bias of the PMT 100. Isolation capacitors 102 are also disposed between each output of the pre-amplifier 104 and the inputs of an amplifier 106 in order to reduce DC offset errors.

Figure 4:
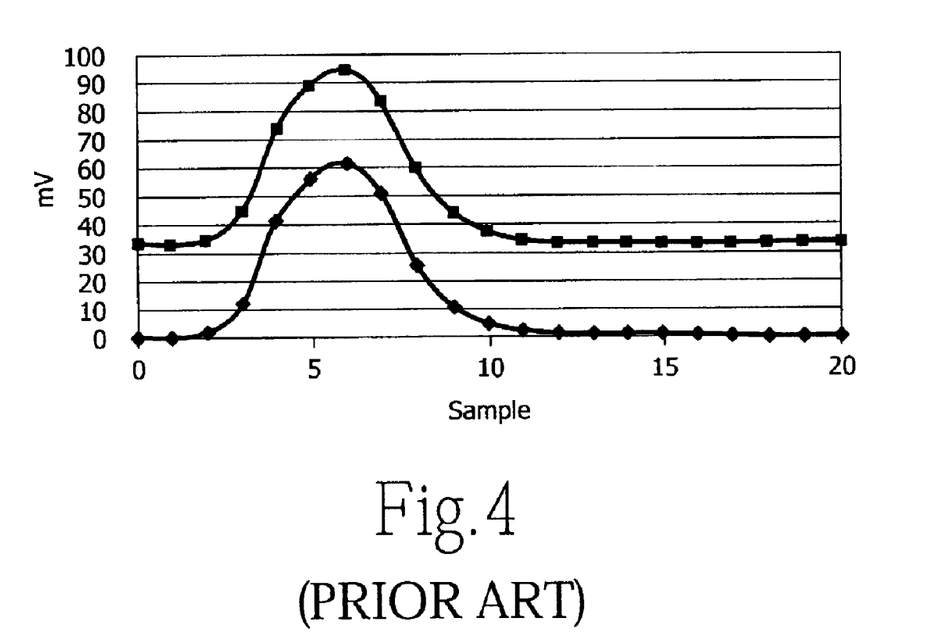
FIG. 4 is a graphical representation of a baseline shift due to charge buildup in the isolation capacitors of FIG. 3 due to the event rate.

Although AC coupling is effective in isolating the high voltage PMT signals from the low voltage processing electronics, the average signal level at the input of the ADCs 108 is dependent on the count rate through the isolation capacitors 102 due to charge buildup. For example, FIG. 4 illustrates a baseline shift due to charge buildup in isolating capacitors. Since the differential pulse height for a mono-energy input is repeatable, the change in average value, the common mode level, with count rate results in an error in pulse height measurement. Because position normalization is also dependent on pulse height measurement, final crystal position used to localize the annihilation is ultimately affected.

It is necessary to determine the baseline prior to an event and correct the baseline to a fixed level. Traditionally, this has been performed by using analog negative feedback baseline correction schemes which correct the baseline when a pulse has not been detected by evidence that a constant fraction discriminator (CFD) has not fired. However, with such a scheme it is possible for the CFD to not register an event if the energy of the pulse is low enough not to trigger the CFD. This results in the negative feedback of the analog baseline circuits attempting to incorrectly adjust the baseline since the error signal used to correct the baseline is derived from an event and not the desired average value.

Other methods have been developed to overcome these and similar problems associated with energy measurement associated with a crystal scintillation event. Typical of the art are those devices disclosed in the following U.S. Patents:

| U.S. Patent No. | Inventor(s) | Issue Date |
| --- | --- | --- |
| 5,585,637 | Bertelsen et al. | Dec. 17, 1996 |
| 5,608,221 | Bertelsen et al. | Mar. 4, 1997 |
| 5,841,140 | McCroskey et al. | Nov. 24, 1998 |
| 6,072,177 | McCroskey et al. | Jun. 6, 2000 |
| 6,160,259 | Petrillo et al. | Dec. 12, 2000 |
| 6,252,232 | McDaniel et al. | Jun. 26, 2001 |
| 6,255,655 | McCroskey et al. | Jul. 3, 2001 |
| 6,291,825 | Scharf et al. | Sep. 18, 2001 |

Also of interest is Takahashi, et al., in "A New Pulse Height Analysis System Based on Fast ADC Digitizing Technique," Conference Record of the Nuclear Science Symposium & Medical Imaging Conference, 1992, Vol. 1, pp. 350–352.

Of these patents, the '140, '177 and 655 patents issued to McCroskey et al., disclose a gamma camera modified to perform PET and Single Photon Emission Computed Tomography (SPECT) studies. These devices utilize SPECT electronics to generate triggering pulse signals for photons indicative of a positron annihilation event which are corrected, on a bundled basis, for position, linearity and uniformity by the same digital processors used by the camera for SPECT studies. While these patents specifically set forth methods to correct for timing delays, McCroskey et al., do not address baseline correction of DC and count rate offsets.

Petrillo et al., in the '259 patent, and Scharf et al., in the '825 patent, disclose a method and apparatus for selectively integrating PMT channel signals in a gamma camera system. In the '259 method, a trigger word is decoded to determine which of multiple PMT channels are affected by a given scintillation event. When two scintillation events overlap both spatially and temporally, only those channels which are affected by both events stop integrating in response to the second event. Pre-pulse pile-up is corrected by removing the tail of a preceding pulse from a current pulse using an approximation of the tail of the preceding pulse based upon the instantaneous energy of the current pulse and the current count rate.

In the '232 patent issued to McDaniel et al., a detector is disclosed as including opposed detector heads having anode signal processors. The anode signal processors perform a sliding box car integration of each PMT anode signal, as well as correct for baseline shifts and pileup from the tails of previous events, vary the length of the box car based on the time between events, and use a peak detection circuit to reduce the dependence of the integrated value on timing differences between the asynchronous events and the synchronous ADC conversion.

Takahashi, et al., discuss a digitizing system using a pulse height analysis system in nuclear spectroscopy, concluding that a technique disclosed therein has a possibility to analyze individual signals with required accuracies and to be used as an advanced signal processing method. It was noted by the authors that one problem is that noted in the present disclosure—that it was often observed that the baseline of the preamplifier output changed greatly due to the tail of the previous pulse. In order to estimate the baseline value under the signal pulse, an averaging method was employed wherein M points of sampled data are summed and averaged. In order to accomplish this method, the summed data is averaged with equally weighted coefficients.

BRIEF SUMMARY OF THE INVENTION

The present invention is a method and apparatus for determining and correcting the baseline of a continuously sampled signal for use in positron emission tomography (PET) is disclosed. The method of the present invention serves to reduce the cost of and improve the performance and reliability of PET. The method of the present invention employs continuous signal sampling to determine the signal level at time t(0) so that an accurate determination of the integrated signal may be calculated, resulting in an accurate energy estimate for an ac-coupled, continuously-sampled signal at various count rates.

The device of the present invention includes a front-end electronics processing channel which consists primarily of an analog CMOS Application Specific Integrated Circuit (ASIC), a bank of Analog-to-Digital Converters (ADCs), a Field Programmable Gate Array (FPGA) based digital sequencer, and two Random Access Memories (RAMs).

The analog CMOS ASIC includes an integrated constant fraction discriminator (CFD) and a time-to-digital converter (TDC). Also included are semi-Gaussian shaped photomultiplier (PMT) channels which are continuously sampled to determine energy on a per channel basis. The processing electronics perform continuous digital integration of the PMT current signals to obtain normalized position and energy for each event.

The position and energy channels utilize a baseline restoration (BLR) algorithm wherein the baseline of the signal pulses are placed at mid-scale by continuously sampling the ADC, thus always making available the past history in discrete steps. By performing an average calculation of the current baseline prior to the associated CFD firing (signifying an event of interest), a correction signal is generated for use in negative feedback control of the baseline. A feedback signal is used to control an analog constant current source across a fixed capacitor to alter the analog baseline to the desired operating point. The baseline voltage offset adjust circuit is controlled by a Gate signal along with an Up/Down control signal to control the baseline.

The CMOS ASIC includes a baseline control circuit wherein signals from the PMTs are amplified and ac-coupled to front-end amplifiers to normalize variations in light yield. The analog CMOS ASIC is used to generate timing information for each event and shape the high bandwidth PMT signals for use in qualifying the energy of each detected event. The CFD generates a time mark signal which indicates the detection of a gamma ray and triggers event processing by the FPGA.

Each analog CMOS ASIC shapes four PMT signals using two-pole low pass filters. Each shaped signal is differentially driven to a continuous sampling ADC in a mode that allows digital baseline restoration with a minimal loss in dynamic range. Each PMT is digitized by a single ADC. PMT gain information is shared between necessary channels so that ADC corrections are performed prior to energy and position calculations.

After the continuous panel setup information has been stored in the analog ASIC and lookup RAMs, the FPGA is programmed with the sequencer logic equations. The FPGA is re-programmable and performs crystal detection, pileup detection, energy qualification, time correction, and baseline restore functions. The FPGA digitally integrates the PMT signals and controls the processing routines. The FPGA is also used to perform setup functions such as loading the analog ASIC registers via an $I_2C$ bus interface, loading the position, energy and time correction lookup tables, as well as determining the event rates for each individual detector area.

Detection by the FPGA of a synchronous time mark from the analog ASIC starts the FPGA and ensures that framing is correct for all detected events. The FPGA controls the ADC mode logic, the digital integration and division for the energy output and the shape discrimination and digital division for the normalized X and Y signals. The FPGA also controls the lookup RAMs for crystal type identification and event location, as well as event energy qualification and time correction. Finally, the FPGA frames the data and sends the event data serially to the next set of event processors.

The RAMs perform energy qualification, determine the event position, and perform event time correction. The events from a continuous detector panel are energy-qualified and time corrected per crystal using a lookup table.

In an alternate method of adjusting the baseline, no negative feedback to the ADC common mode output is used. In the alternate method, the measured baseline is subtracted from the pulse height measurement. In a simplified example, placing the baseline near the A/D mid-scale allows the baseline to shift in either direction without loss of measurement. The measured baseline is then subtracted from the measured pulse height of each sample and the energy of the pulse is determined from the integral of the samples. Alternately, the baseline may be adjusted to below mid-scale to allow a greater dynamic range to be utilized for unipolar shaping.

The method and apparatus of the present invention is useful in ac-coupled systems utilizing a wide variety of scintillation materials. Such scintillation materials include, but are not limited to, LYSO, LGSO, GSO, BGO and LSO. Further, ADC sampling rates and energy shaping filter time constants may be adapted as required for various environments in which the present invention is employed. To wit, specific sampling rates and energy shaping filter time constants are disclosed as exemplary of such that have been found acceptable.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A method for determining and correcting the baseline of a continuously sampled signal for use in positron emission tomography (PET) is disclosed. The method of the present invention serves to reduce the cost of and improve the performance and reliability of PET. The method of the present invention employs continuous signal sampling to determine the average signal level for each event at time t(0) so that an accurate determination of the integrated signal may be calculated. The result is an accurate energy estimate for ac-coupled, continuously-sampled photomultiplier tube (PMT) signals at various count rates. A gamma ray from a positron annihilation interacts with a scintillator crystal such as LSO, which produces light output proportional to the absorbed gamma energy. The light output is sensed by a PMT which produces a current signal which is shaped and digitally sampled to accurately determine the total energy relative to each event. An apparatus for performing the method of the present invention is also disclosed.

Figure 5:
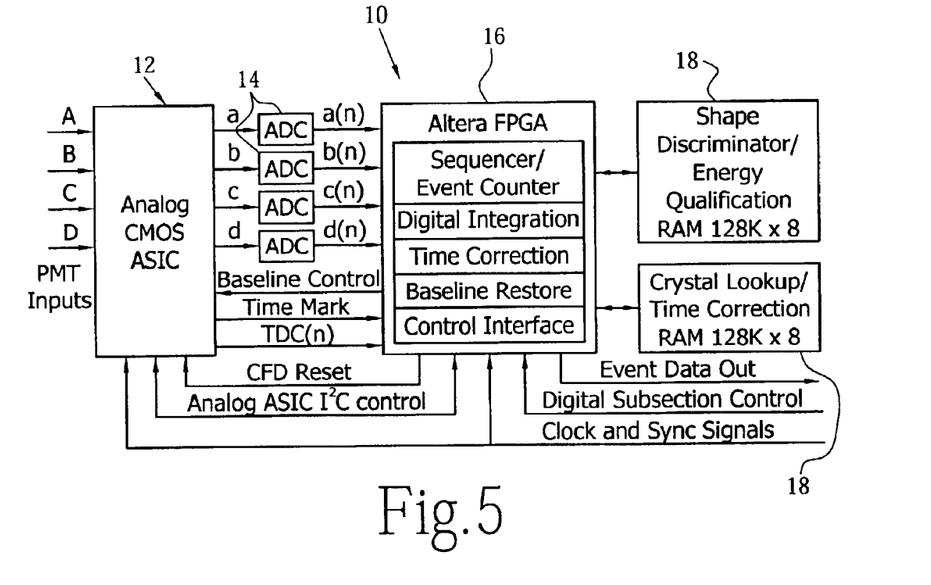
FIG. 5 is a block diagram of the front-end electronics processing channel incorporating several features of the device of the present invention.

The device of the present invention uses a combination of digital and analog electronics techniques to determine the baseline prior to an event and correct the baseline to a fixed level. Included is a front-end electronics processing channel 10, such as illustrated in FIG. 5, consisting primarily of four functional blocks. These functional blocks include an analog CMOS Application Specific Integrated Circuit (ASIC) 12, a bank of Analog-to-Digital Converters (ADCs) 14, a Field Programmable Gate Array (FPGA) based digital sequencer 16, and two Random Access Memories (RAMs) 18.

Figure 6:
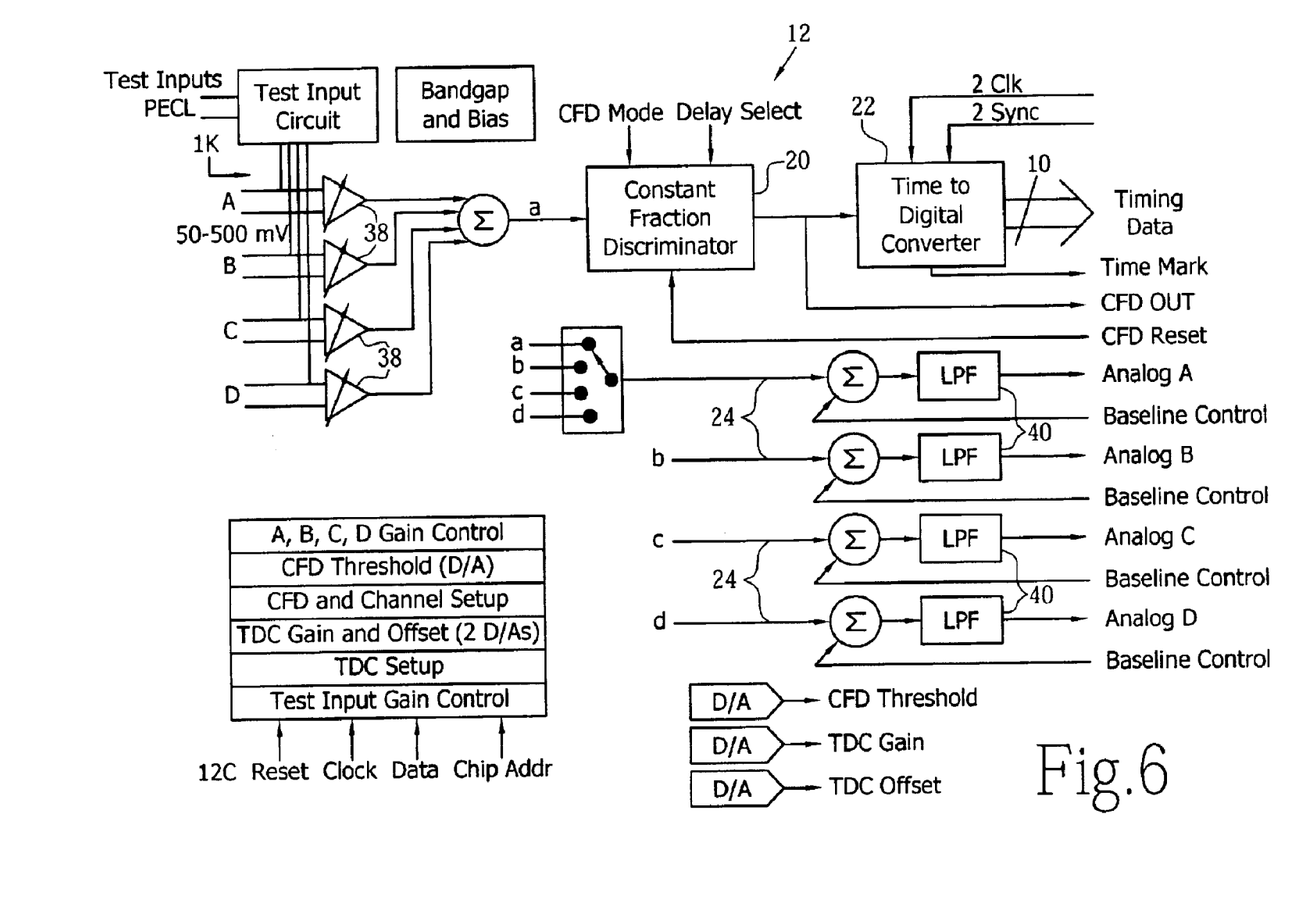
FIG. 6 is a block diagram of a CMOS ASIC incorporated in the front-end electronics of FIG. 5.

FIG. 6 is a block diagram of a CMOS ASIC 12 used in the present invention. The illustrated analog ASIC 12 includes an integrated constant fraction discriminator (CFD) 20 and a time-to-digital converter (TDC) 22 with intrinsic minimum timing resolution of 312 ps. Also included are semi-Gaussian shaped photomultiplier (PMT) channels 24 which are continuously sampled to determine energy on an area. The processing electronics perform continuous digital integration of the PMT signals to obtain normalized position and energy. It will be understood that the present invention is not limited to either this configuration or timing resolution.

Figure 7:
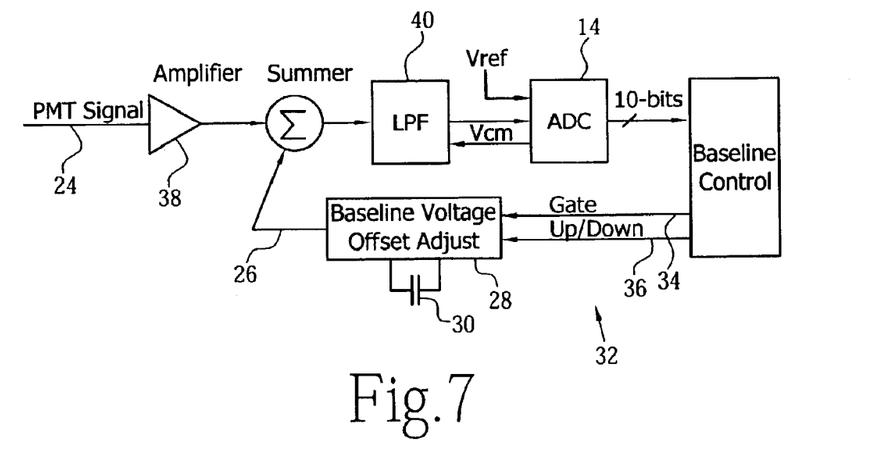
FIG. 7 is a schematic illustration of the baseline control circuit in accordance with the present invention.

The CMOS ASIC 12 architecture of the present invention eliminates gated baseline restoration, as the CFD 20 utilizes a continuous baseline restoration (BLR). The baseline of the shaped PMT signal pulses are ideally placed at mid-scale by continuously sampling the ADC 14. As a result, the past history is always available. By performing an average calculation of the current baseline prior to the associated CFD 20 firing, a correction signal is generated for use in negative feedback control of the baseline. As illustrated in FIG. 7, a feedback signal 26 is used to control an analog constant current source 28 across a fixed capacitor 30 to alter the baseline to the desired operating point. The baseline voltage offset adjust circuit 32 is controlled by a Gate signal 34 along with an Up/Down control signal 36 to control the baseline. Using the present architecture, the continuous CFD 20 BLR function allows channel processing times of approximately 100 nanoseconds. Because the energy channels utilize continuous sampling ADCs 14, energy channel dc-correction is estimated by examining the baseline history immediately prior to an event. The CMOS ASIC 12 allows for additional baseline correction via digital pulse correction, which alters the energy channel offset voltage by utilizing constant charging currents through a fixed off-chip capacitor.

Again referring to FIG. 7, which is a block diagram of a portion of the CMOS ASIC 12 including a baseline control circuit incorporated therein, signals 24 from the PMTs are amplified and ac-coupled to the analog ASIC front-end amplifiers 38 to normalize variations in light yield. The analog ASIC 12 is used to generate timing information for each event and shape the high bandwidth PMT signals 24 for use in qualifying the energy of each detected event. The CFD 20 generates a time mark signal which indicates the detection of a gamma ray and triggers event processing by the FPGA 16.

Figure 8:
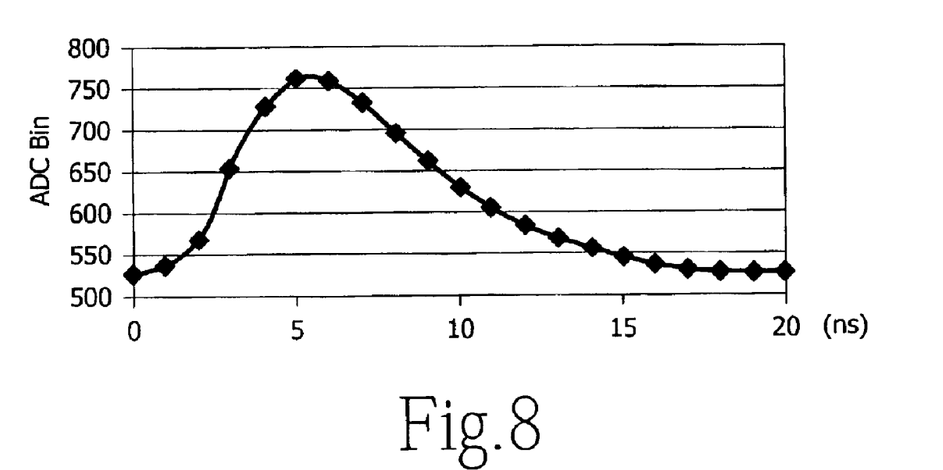
FIG. 8 is a graphical illustration of raw ADC output of a typical signal from the ASIC shaping filter sampled at 100 MHz using the method and apparatus of the present invention.

Referring again to FIG. 5, each analog ASIC 12 shapes four PMT signals 24 using two-pole low pass filters 40. Each shaped signal is differentially driven to a continuous sampling ADC 14 in a mode that allows digital baseline restoration with a minimal loss in dynamic range. The overall scanner architecture is designed such that each PMT is digitized by a single ADC 14. PMT gain information is shared between necessary continuous panel channels so that ADC corrections are performed prior to energy and position calculations. FIG. 8 illustrates raw ADC output of a typical signal from the ASIC shaping filter sampled at 100 MHz. The signal baseline is set near the mid-range of the differential ADC 14 at bin 530, but is not yet optimized for full dynamic range. In one application of the present invention, differential ADCs 14 having a differential range of 2 volts (+1 v full scale positive, −1 v full scale negative) were used. A 15 ns two-pole low pass filter 40 is used to shape the PMT signals 24. While differential ADCs 14 are used in this example, the present invention is not limited to differential ADCs 14.

After the continuous panel setup information has been stored in the analog CMOS ASIC 12 and lookup RAMs 18, the FPGA 16 is programmed with the sequencer logic equations. The FPGA 16 is re-programmable and performs crystal detection, pileup detection, energy qualification, time correction, and baseline restore functions. The FPGA 16 digitally integrates the PMT signals 24 and controls the processing routines. The FPGA 16 is also used to perform setup functions such as loading the analog ASIC registers via an I$_2$C bus interface, loading the position, energy and time correction lookup tables, as well as determining the event rates for each individual continuous detector panel.

Detection by the FPGA 16 of a synchronous time mark from the analog ASIC 12 starts the FPGA 16 and ensures that framing is correct for all detected events. The FPGA 16 controls the ADC mode logic, the digital integration and division for the energy output and the shape discrimination and digital division for the normalized X and Y signals. The FPGA 16 also controls the lookup RAMs 18 for crystal type identification and event location, as well as event energy qualification and time correction. Finally, the FPGA 16 frames the data and sends the event data serially to the next set of event processors.

The RAMs 18 perform energy qualification, determine the event position, and perform event time correction. The events from a continuous detector panel are energy-qualified and time corrected per crystal using a lookup table.

Figure 9:
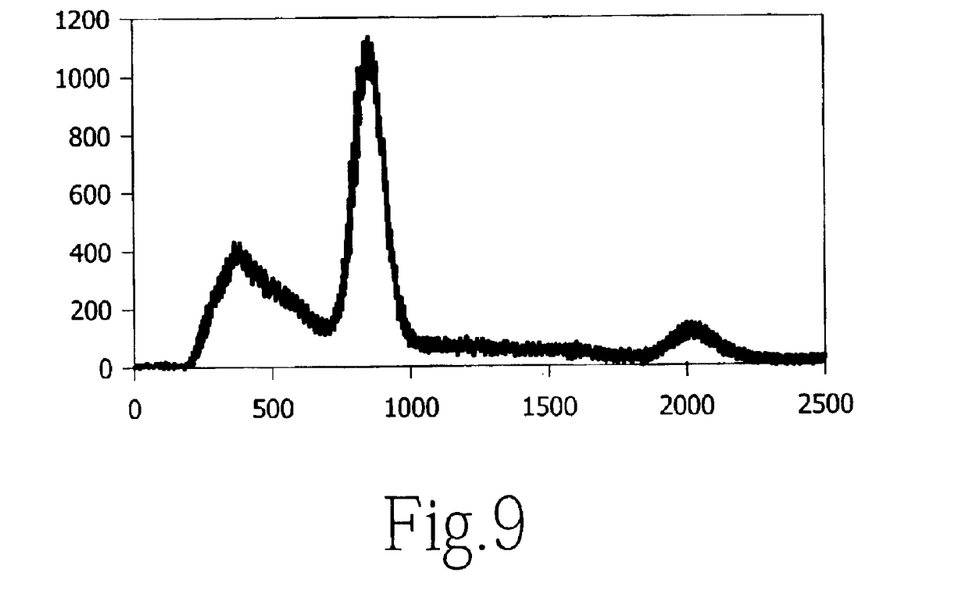
FIG. 9 is a graphical illustration of a measured energy histogram for a single LSO crystal/PMT with a Na-22 source using 16 contiguous samples by means of the method and apparatus of the present invention.

FIG. 9 illustrates a measured energy histogram for a single LSO crystal/PMT with a Na-22 source using 16 contiguous samples. The overall LSO crystal energy resolution at a sample rate of 50 MHz has been found to be 17.6%. At sample rates of 100 MHz and 250 MHz, the energy resolution was found to be 16.0%. The overall energy resolution of 16% compared well to the crystal energy resolution measured using analog based NIM electronics and an independent MCA. The energy resolution shown illustrates that minimal degradation in energy resolution added by the digital electronics processing.

Figure 10:
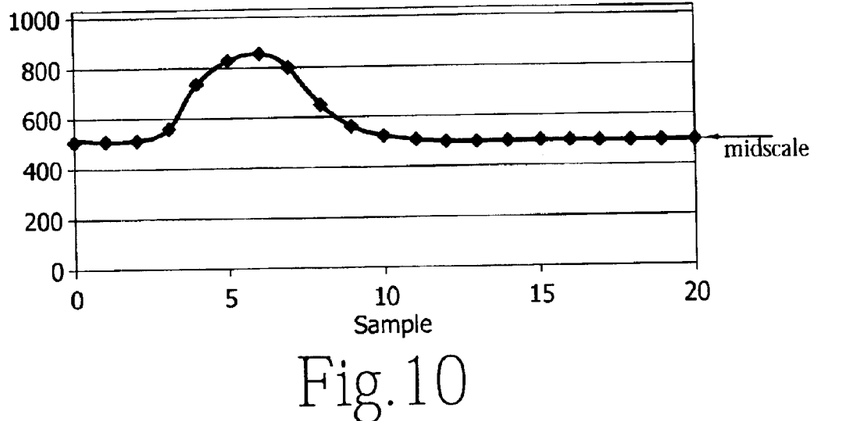
FIG. 10 is a graphical illustration of a sampled signal wherein the baseline is set at an approximate mid-scale of the analog-to-digital converters.

In an alternate method of adjusting the baseline, no negative feedback is used. In the alternate method, the measured baseline is subtracted from the pulse height measurement. Setting the baseline near the A/D mid-scale allows the baseline to shift in either direction without loss of measurement. As illustrated in FIG. 10, the measured baseline is set at approximately mid-scale. The measured baseline is then subtracted from the measured pulse height and the energy of the pulse is determined from the integral of the samples.

Figure 11:
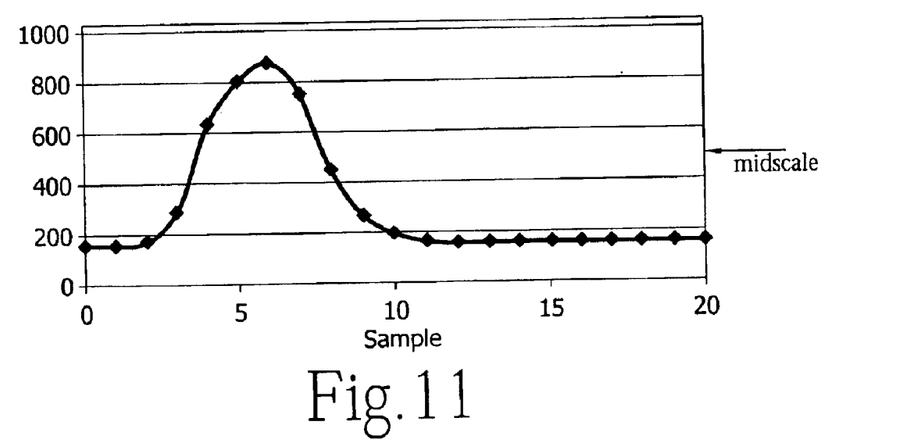
FIG. 11 is a graphical illustration of a sampled signal wherein the baseline is adjusted to below the mid-scale of the analog-to-digital converters to allow utilization of a greater dynamic range.

While the alternate method has described the baseline, being set at mid-scale, it is anticipated that the other advantages may be attained by setting the baseline away from mid-scale so that the full dynamic range of the ADCs 14 may be used. For example, as illustrated in FIG. 11, the baseline is adjusted to below mid-scale, thereby allowing a greater dynamic range to be utilized.

The method and apparatus of the present invention, as described, is useful in ac-coupled systems utilizing a wide variety of scintillation materials. Such scintillation materials include, but are not limited to, LYSO, LGSO, GSO and LSO. Further, ADC sampling rates and energy shaping filter time constants may be adapted as required for various environments in which the present invention is employed. To wit, specific sampling rates and energy shaping filter time constants are disclosed as exemplary of such that have been found acceptable.

From the foregoing description, it will be recognized by those skilled in the art that a method for determining and correcting the baseline of a continuously sampled signal for use in PET offering advantages over the prior art has been provided. Namely, the method of the present invention serves to reduce the cost of and improve the performance and reliability of PET. The method and apparatus of the present invention generates an accurate energy estimate for an ac-coupled, continuously-sampled signal at various count rates.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of the general inventive concept.

What is claimed is:

1. A device for determining and correcting the baseline of a continuously sampled signal for use in positron emission tomography (PET), said device comprising a front-end electronics processing channel for performing continuous digital integration of photomultiplier (PMT) signals to obtain normalized position and energy, said electronics processing channel including:

an analog CMOS Application Specific Integrated Circuit (ASIC) for shaping the PMT signals and performing continuous baseline restoration;

a plurality of Analog-to-Digital Converters (ADCs) for digitizing the PMT signals;

a digital sequencer for performing crystal detection, pileup detection, energy qualification, time correction, and baseline restore functions; and a plurality of Random Access Memories (RAMs) for performing energy qualification, determining event position, and performing event time correction.

2. The device of claim 1 wherein said analog CMOS ASIC includes an integrated constant fraction discriminator (CFD), a time-to-digital converter (TDC), and semi-Gaussian shaped PMT channels, said PMT channels being continuously sampled to determine energy on a per area basis.

3. The device of claim 2 wherein said CFD utilizes a continuous baseline restoration (BLR), wherein an initial value of pulses of said PMT signals is selected by continuously sampling said ADCs, wherein an average calculation of the current baseline prior to said pulses is performed, and a correction signal is generated for use in negative feedback control of the baseline.

4. The device of claim 3 wherein said CMOS ASIC further includes a baseline control circuit, wherein said PMT signals are amplified and ac-coupled to a plurality of front-end amplifiers to normalize variations in light yield, said analog CMOS ASIC being used to generate timing information for each event and shape said PMT signals for use in qualifying energy from each event, said CFD generating a time mark signal indicating detection of a gamma ray and triggering event processing by said digital sequencer.

5. The device of claim 2 wherein said analog CMOS ASIC further includes two low-pass filters, said two low-pass filters for shaping four said PMT signals.

6. The device of claim 1 wherein each of said plurality of ADCs is provided for digitizing one PMT signal.

7. The device of claim 1 wherein said digital sequencer is a Field Programmable Gate Array (FPGA).

8. The device of claim 7 wherein said FPGA is re-programmable, and wherein said FPGA is further provided for digitally integrating the PMT signals, controlling processing routines, performing setup functions including at least loading registers within said analog CMOS ASIC, loading position, energy and time correction lookup tables, and determining event rates.

9. The device of claim 1 wherein said plurality of RAMs include a lookup table for energy-qualifying and time-correcting events from a continuous detector panel per crystal.

10. A method for determining and correcting the baseline of a continuously sampled signal for use in positron emission tomography (PET), said method utilizing a device including front-end electronics processing channel for performing continuous digital integration of photomultiplier (PMT) signals to obtain normalized position and energy, said electronics processing channel including an analog CMOS Application Specific Integrated Circuit (ASIC) for shaping the PMT signals and performing continuous baseline restoration, a plurality of Analog-to-Digital Converters (ADCs) for digitizing the PMT signals, a digital sequencer for performing crystal detection, pileup detection, energy qualification, time correction, and baseline restore functions, and a plurality of Random Access Memories (RAMs) for performing energy qualification, determining event position, and performing event time correction, said method comprising the steps of:
  (a) sampling continuously at least one PMT signal to determine energy on a per area basis;
  (b) setting a current baseline of said PMT signal at a selected value;
  (c) shaping said PMT signal using said analog CMOS ASIC;
  (d) generating a correction signal by determining an average of previous values of said current baseline;
  (e) altering said current baseline using said correction signal.

11. The method of claim 10 wherein said analog CMOS ASIC includes at least one front-end amplifier and a Constant Fraction Discriminator (CFD), said step of shaping said PMT signal includes the steps of:
  (i) amplifying said PMT signals to achieve amplified PMT signals;
  (ii) ac-coupling the amplified PMT signals to said at least one front-end amplifier whereby variations in light yield are normalized;
  (iii) generating timing information; and
  (iv) generating a time mark signal by said CFD to indicate detection of a gamma ray and to trigger event processing by said digital sequencer.

12. The method of claim 10 after said step of altering said current baseline, further comprising the step of integrating said PMT signal by said digital sequencer.

13. The method of claim 10 wherein said step of altering said current baseline is accomplished using negative feedback.

14. The method of claim 10 wherein said step of altering said current baseline includes the steps of
  (i) subtracting a measured baseline from a pulse height measurement; and
  (ii) setting the baseline near a mid-scale of said plurality of ADCs, whereby the baseline to shift in either direction without loss of measurement.

15. The method of claim 10 wherein said step of altering said current baseline includes the steps of
  (i) subtracting a measured baseline from a pulse height measurement; and
  (ii) setting the baseline below a mid-scale of said plurality of ADCs,
whereby the baseline to shift in either direction without loss of measurement.

16. The method of claim 10 wherein said device further includes a fixed capacitor, said method further comprising the step of altering an energy channel offset voltage using constant charging currents through said capacitor to achieve additional baseline correction.

* * * * *